United States Patent

Narayanan

[11] 3,976,657
[45] Aug. 24, 1976

[54] 3-HETERO-5-SUBSTITUTED AMINOPHENYLOXADIAZOLES

[75] Inventor: Venkatachala Lakshmi Narayanan, Hightstown, N.J.

[73] Assignee: E. R. Squibb & Sons, Inc., Princeton, N.J.

[22] Filed: Mar. 17, 1975

[21] Appl. No.: 559,181

[52] U.S. Cl............................ 260/307 G; 260/326.9; 260/329 AM; 260/347.7; 424/272
[51] Int. Cl.².................................. C07D 271/06
[58] Field of Search............................ 260/307 G

[56] References Cited
UNITED STATES PATENTS 3,211,742  10/1965  Lenaers ............................ 260/307

Primary Examiner—Raymond V. Rush
Attorney, Agent, or Firm—Lawrence S. Levinson; Merle J. Smith; Donald J. Barrack

[57] ABSTRACT

Compounds having the structure

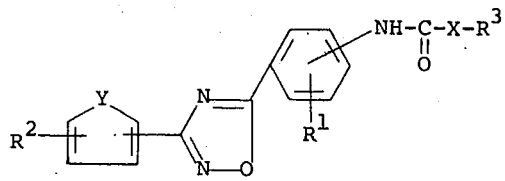

wherein $R^1$ is hydrogen, alkyl, aryl, halo, alkoxy or aryloxy; $R^2$ is hydrogen or methyl; $R^3$ is alkyl, haloalkyl, cycloalkyl or aryl; X is oxygen or sulfur; and Y is oxygen, sulfur or =NH, have useful physiological activity.

17 Claims, No Drawings

3-HETERO-5-SUBSTITUTED AMINOPHENYLOXADIAZOLES

BRIEF DESCRIPTION OF THE INVENTION

Compounds having the structure

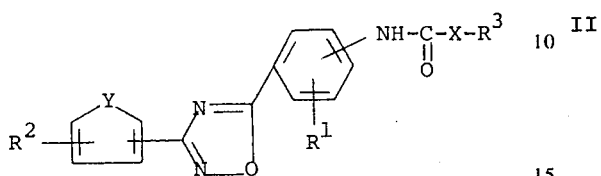

have useful physiological activity.

In formula I, and throughout the specification, the symbols are as defined below:

$R^1$ is hydrogen, alkyl, aryl, halo, alkoxy, or aryloxy;
$R^2$ is hydrogen or methyl;
$R^3$ is alkyl, haloalkyl, cycloalkyl or aryl;
X is oxygen or sulfur; and
Y is oxygen, sulfur or =NH.

The term "alkyl", as used throughout the specification, refers to alkyl groups having 1 to 7 carbon atoms. Alkyl groups having 1 to 4 carbon atoms are preferred.

The term "aryl", as used throughout the specification, refers to phenyl or phenyl substituted with one or more halo, alkyl or alkoxy groups. Phenyl and monosubstituted phenyl are preferred.

The term "halo", as used throughout the specification, refers to fluorine, chlorine, bromine and iodine; chlorine and bromine are the preferred halogens.

The term "alkoxy", as used throughout the specification, refers to a group having the formula alkyl-O-, wherein alkyl is as defined above.

The term "aryloxy", as used throughout the specification, refers to a group having the formula aryl-O-, wherein aryl is as defined above.

The term "haloalkyl", as used throughout the specification, refers to an alkyl group substituted with one or more halogen atoms. The preferred haloalkyl group is trichloroethyl.

The term "cycloalkyl", as used throughout the specification, refers to saturated hydrocarbon rings having 3 to 6 carbon atoms, i.e., cyclopropyl, cyclobutyl, cyclopentyl and cyclohexyl.

DETAILED DESCRIPTION OF THE INVENTION

The substituted aminophenyloxadiazoles of formula I have activity against gram-positive bacteria and fungi, and are useful in mammalian species for the treatment and prevention of (a) superficial dermatoses, bacterial or fungal diseases due to species of Staphylococcus, Streptococcus, Corynebacterium, Erysipelothrix, Candida, Trichophyton, Microsporum and Epidermophyton, (b) deep mycoses, fungal diseases due to Candida, Cryptococcus, Blastomyces, Histoplsma and similar organisms, and (c) thrush, fungal disease due to Candida species, principally Candida albicans.

In general, in the compounds of this invention exhibit antibacterial and antifungal activity when applied as a 0.5-2.0% cream or ointment to the skin of an affected mammal for 2 weeks or more; given orally in daily doses of about 10-200 milligrams per kilogram of body weight; given by injection in daily doses of about 10-50 milligrams per kilogram of body weight; or given intravaginally. The compounds are formulated for all forms of administration using conventional pharmaceutical techniques.

The compounds of formula I can be prepared by reacting an aminophenyloxadiazole having the formula

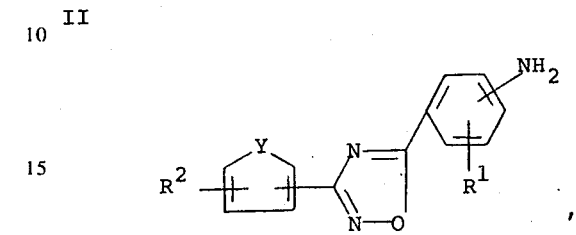

with a compound having the formula

wherein the halogen atom is preferably chlorine. The reaction can be run in an organic solvent such as an aromatic hydrocarbon, e.g. benzene, toluene, or the like, an ether such as diethyl ether, tetrahydrofuran, dioxane or the like, or acetonitrile, in the presence of an acid binding agent such as an alkali metal carbonate or a tertiary amine such as triethylamine or the like. It is also possible to employ a solvent which will serve as an acid binding agent as well, e.g. pyridine, picolines and others. While reaction conditions are not critical, the reaction will most preferably be run at the reflux temperature of the solvent.

The aminophenyloxadiazoles of formula II can be prepared using as starting materials nitrobenzoyl halides (preferably nitrobenzoyl chlorides) having the formula

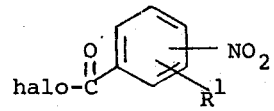

and amidoximes having the formula

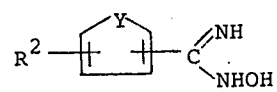

The nitrobenzoyl halides of formula IV can be prepared from the corresponding nitrobenzoic acid using procedures well known in the art. The amidoximes of formula V can be prepared by reacting a nitrile having the formula

VI

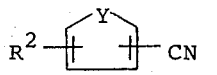

with an acid salt of hydroxylamine, e.g. the hydrochloride or sulfate, in the presence of an acid acceptor such as an alkali metal carbonate. The reaction is preferably conducted in a lower alkanol solvent, optionally in the presence of water. Reaction conditions are not critical and the reaction can be run at room temperature or at the reflux temperature of the solvent.

Reaction of a nitrobenzoyl halide of formula IV with an amidoxime of formula V yields a nitrophenyloxadiazole having the formula

VII

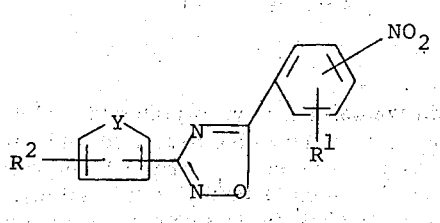

The reaction can be run in an inert organic solvent, e.g. benzene, toluene, dioxane, tetrahydrofuran, and others, preferably, in the presence of a catalytic amount of boron trifluoride etherate. The reaction proceeds best when it is run at elevated temperatures.

A nitrophenyloxadiazole of formula VII can be reduced to the corresponding aminophenyloxadiazole of formula II using conventional techniques. The preferred procedure is to run the reduction reaction using gaseous hydrogen in the presence of a palladium catalyst on charcoal and two to five equivalents of a mineral acid, such as hydrochloric acid.

The compounds of formula I wherein $R^1$ is halogen are preferred, and those wherein $R^1$ is chlorine are most preferred.

The compounds of formula I wherein $R^2$ is hydrogen are preferred.

The following examples are specific embodiments of this invention.

EXAMPLE 1

[2-Chloro-5-[3-(2-furanyl)-1,2,4-oxadiazol-5-yl]phenyl]carbamic acid, methyl ester

A.

5-(4-Chloro-3-nitrophenyl)-3-(2-furanyl)-1,2,4-oxadiazole

To a solution of 2-furancarboxamidoxime (8.8 g) in 300 ml of dry dioxane a solution of 4-chloro-3-nitrobenzoyl chloride (prepared from 14.1 g of 4-chloro-3-nitrobenzoic acid and 16.7 g of thionyl chloride) in 50 ml of dioxane which contains 1 ml of boron trifluoride etherate is added. The resulting suspension is refluxed for 16 hours. The solution is evaporated to dryness and the crude product is decolorized. A single recrystallization from absolute ethanol yields 10.8 g of the title compound, melting point 136°–137.5°C.

B.

5-(3-Amino-4-chlorophenyl)-3-(2-furanyl)-1,2,4-oxadiazole

To a slurry of 32.1 g of 5-(4-chloro-3-nitrophenyl)-3-(2-furanyl)-1,23,4-oxadiazole in 800 ml of absolute ethanol and 37.4 ml of concentrated hydrochloric acid, is added a slurry of 0.3 g of 10% palladium on charcoal in ethanol. The mixture is hydrogenated for 3 hours on a Parr hydrogenator at 45 p.s.i. The insoluble amine hydrochloride is filtered and washed with ethanol and the filtrate is concentrated to dryness. The residue and the precipitate are combined and treated with a 20% potassium carbonate solution in the presence of chloroform. The aqueous phase is extracted four times with chloroform and the extracts are dried, using magnesium sulfate, filtered and concentrated to dryness yielding 22 g of crude product. This residue is recrystallized from acetone/water yielding 15.2 g of the title compound in 4 crops.

C.

[2-Chloro-5-[3-(2-furanyl)-1,2,4-oxadiazol-5-yl]phenyl]carbamic acid, methyl ester To a mixture of 5-(3-amino-4-chlorophenyl)-3-(2-furanyl)-1,2,4-oxadiazole (1.35 g) and 1.05 g of potassium carbonate in 30 ml of dioxane, 0.75 g of methyl chloroformate is added. The resulting mixture is heated at reflux for 16 hours, concentrated to dryness and the residue placed on an alumina column. The product is eluted with benzene to yield 0.45 g of the title compound, melting point 200°–201°C.

EXAMPLE 2

[2-Chloro-5-[3-(2-furanyl)-1,2,4-oxadiazol-5-yl]phenyl]carbamic acid, 2,2,2-trichloroethyl ester To a mixture of 5-(3-amino-4-chlorophenyl)-3-(2-furanyl)-1,2,4-oxadiazole (0.75 g) and 0.58 g of potassium carbonate in 25 ml of dioxane is added 0.80 g of 2,2,2-trichloroethyl chloroformate. The resulting mixture is heated at reflux for 2 hours, and concentrated to dryness. 50 ml of water is added to the residue and the resulting mixture is extracted three times with chloroform. The extracts are dried over magnesium sulfate, filtered and concentrated to dryness. The residue is absorbed on an alumina column and eluted with benzene to give 0.50 g of the title compound, melting point 114°–116°C.

EXAMPLE 3

[2-Chloro-5-[3-(2-furanyl)-1,2,4-oxadiazol-5-yl]phenyl]carbamic acid, phenyl ester To a mixture of 5-(3-amino-4-chlorophenyl)-3-(2-furanyl)-1,2,4-oxadiazole (0.75 and 0.58 g of potassium carbonate in 30 ml of dioxane is added 0.94 g of phenylchloroformate. The resulting mixture is heated at reflux for 2 hours and concentrated to dryness. 50 ml of water is added to the residue and the mixture extracted three times with chloroform. The extracts are dried over magnesium sulfate, filtered and concentrated. The residue is recrystallized from benzene to yield 0.62 g of the title compound, melting point 177°–178°C.

EXAMPLE 4

[3-Chloro-4-[3-(2-furanyl)-1,2,4-oxadiazol-5-yl]phenyl]carbamic acid, phenyl ester

A.

5-(2-Chloro-4-nitrophenyl)-3-(2-furanyl)-1,2,4-oxadiazole

To a solution of 2-furancarboxamidoxime (8.8 g) in 300 ml of dry dioxane is added a solution of 2-chloro-4-nitrobenzoyl chloride (prepared from 14.1 g of 2-chloro-4-nitrobenzoic acid and 16.7 g of thionyl chloride) in 50 ml of dioxane containing 1 ml of boron trifluoride etherate. The resulting suspension is refluxed for 16 hours and the solution is evaporated to dryness. The crude product is decolorized. A single recrystallization from absolute ethanol yields 10.1 g of the title compound, melting point 124°–125°C.

B.

5-(4-Amino-2-chlorophenyl)-3-(2-furanyl)-1,2,4-oxadiazole

To a slurry of 28.8 g of 5-(2-chloro-4-nitrophenyl)-3-(2-furanyl)-1,2,4-oxadiazole in 600 ml of absolute ethanol and 34 ml of hydrochloric acid is added a slurry of 2.0 g of 10% palladium on charcoal in ethanol. The mixture is hydrogenated in a Parr hydrogenator at 45 p.s.i. for 3 hours. The insoluble amine hydrochloride is filtered and washed with ethanol. The filtrate is concentrated to dryness and the residue and precipitate are combined and treated with a solution of 20% potassium carbonate in the presence of chloroform. The phases are separated and the aqueous phases extracted three times with 300 ml of chloroform. The organic phases are dried over magnesium sulfate, filtered and concentrated to dryness yielding 20 g of crude product. Recrystallization from acetone/water yields 14.2 g of the title compound in 2 crops, melting point 175°–176.5°C.

C.

[3-Chloro-4-[3-(2-furanyl)-1,2,4-oxadiazol-5-yl]phenyl]carbamic acid, phenyl ester To a mixture of 5-(4-amino-2-chlorophenyl)-3-(2-furanyl)-1,2,4-oxadiazole (0.75 g) and 0.56 g of potassium carbonate in 30 ml of dioxane is added 0.94 g of phenyl chloroformate. The resulting mixture is heated at reflux for 2 hours and concentrated to dryness. 50 ml of water is added to the residue and the resulting mixture is extracted three times with 300 ml of chloroform. The residue is recrystallized from benzene to yield 0.75 g of the title compound, melting point 184°–185.5°C.

EXAMPLE 5

[3-Chloro-4-[3-(2-furanyl)-1,2,4-oxadiazol-5-yl]phenyl]carbamic acid, 2,2,2-trichloroethyl ester 2,2,2-Trichloroethyl chloroformate (1.56 g) is added to a mixture of 1.05 g of potassium carbonate and 1.3 g of 5-(4-amino-2-chlorophenyl)-3-(2-furanyl)-1,2,4-oxadiazole in 30 ml of dioxane. The mixture is heated at reflux for 2 hours and concentrated to dryness. The residue is partitioned between water and chloroform and the aqueous layer is extracted twice with chloroform. The combined chloroform extract is dried, filtered and concentrated to yield the crude product. Recrystallization from benzene/dioxane yields 1.2 g of the title compound, melting point 219°–220°C.

EXAMPLES 6–13

Following the procedure of example 1, but substituting the compound listed in column I for 4-chloro-3-nitrobenzoyl chloride, the compound listed in column II for 2-furancarboxamidoxime, and he compound listed in column III for methyl chloroformate, the compound listed in column IV is obtained.

| Example | Column I | Column II | Column III | Column IV |
|---|---|---|---|---|
| 6 | 3-nitrobenzoyl chloride | 3-furancarboxamidoxime | cyclopropyl chloroformate | [3-[3-(3-furanyl)-1,2,4-oxadiazol-5-yl]phenyl]carbamic acid, cyclopropyl ester |
| 7 | 4-methyl-3-nitrobenzoyl chloride | 2-thiophenecarboxamidoxime | 2-chlorophenyl chloroformate | [2-methyl-5-[3-(2-thienyl)-1,2,4-oxadiazol-5-yl]phenyl]carbamic acid, 2-chlorophenyl ester |
| 8 | 3-ethyl-2-nitrobenzoyl chloride | 2-pyrrolecarboxamidoxime | 3-chloropropyl chloroformate | [6-ethyl-2-[3-(1H-pyrrol-2-yl)-1,2,4-oxadiazol-5-yl]phenyl]carbamic acid, 3-chloropropyl ester |
| 9 | 2-methoxy-4-nitrobenzoyl chloride | 2-(3-methylfuran)carboxamidoxime | phenyl chloroformate | [3-methoxy-4-[3-[2-(3-methylfuranyl)]1,2,4-oxadiazol-5-yl]phenyl]carbamic acid, phenyl ester |
| 10 | 4-phenyloxy-3-nitrobenzoyl chloride | 3-(2-methylthiophene)carboxamideoxime | trifluoromethyl chloroformate | [2-phenyloxy-5-[3-[3-(2-methylthienyl)]1,2,4-oxadiazol-5-yl]phenyl]carbamic acid, trifluoromethyl ester |
| 11 | 3-nitrobenzoyl chloride | 3-furancarboxamidoxime | cyclohexyl chlorothioformate | [3-[3-(3-furanyl)-1,2,4-oxadiazol-5-yl]phenyl]thiocarbamic acid, cyclohexyl ester |
| 12 | 4-chloro-3-nitrobenzoyl chloride | 2-thiophenecarboxamidoxime | methyl chlorothioformate | [2-chloro-5-[3-(2-thienyl)-1,2,4-oxadiazol-5-yl]phenyl]thiocarbamic acid, methyl ester |
| 13 | 4-bromo-3-nitrobenzoyl chloride | 3-pyrrolecarboxamidoxime | phenyl chlorothioformate | [2-bromo-5-[3-(1H-pyrrol-3-yl)-1,2,4-oxadiazol-5-yl]phenyl]thiocarbamic acid, phenyl ester |

What is claimed is:

1. A compound having the formula

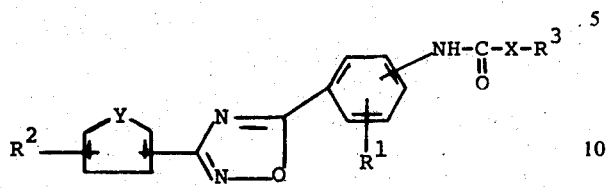

wherein R¹ is hydrogen, alkyl, aryl halo, alkoxy or aryloxy; R² is hydrogen or methyl; R³ is alkyl, haloalkyl, cycloalkyl or aryl; X is oxygen or sulfur; and Y is oxygen, sulfur or =NH; wherein the terms alkyl and alkoxy refer to groups having 1 to 7 carbon atoms; the term cycloalkyl refers to groups having 3 to 6 carbon atoms; and the term aryl refers to phenyl or phenyl monosubstituted with a halo, alkyl or alkoxy group, wherein alkyl and alkoxy are defined as above.

2. A compound in accordance with claim 1 having the formula

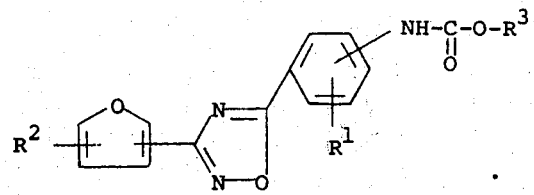

3. A compound in accordance with claim 1 having the formula

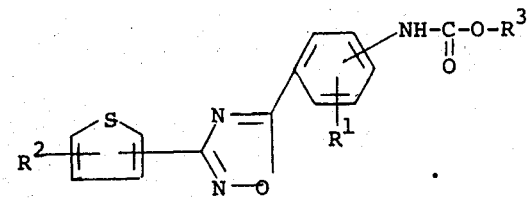

4. A compound in accordance with claim 1 having the formula

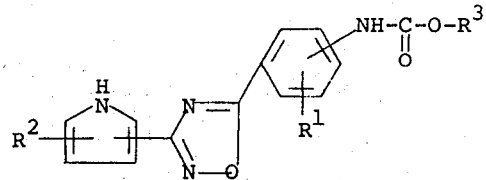

5. A compound in accordance with claim 1 wherein X is oxygen.

6. A compound in accordance with claim 1 wherein R¹ is chlorine.

7. A compound in accordance with claim 1 wherein R² is hydrogen.

8. A compound in accordance with claim 1 wherein R³ is alkyl.

9. A compound in accordance with claim 1 wherein R³ is haloalkyl.

10. A compound in accordance with claim 9 wherein R³ is trichloroethyl.

11. A compound in accordance with claim 1 wherein R³ is aryl.

12. A compound in accordance with claim 11 wherein R³ is phenyl.

13. The compound in accordance with claim 1 having the name [2-chloro-5-[3-(2-furanyl)-1,2,4-oxadiazol-5-yl]phenyl]carbamic acid, methyl ester.

14. The compound in accordance with claim 1 having the name [2-chloro-5-[3-(2-furanyl)-1,2,4-oxadiazol-5-yl]phenyl]carbamic acid, 2,2,2-trichloroethyl ester.

15. The compound in accordance with claim 1 having the name [2-chloro-5-[3-(2-furanyl)-1,2,4-oxadiazol-5-yl]phenyl]carbamic acid, phenyl ester.

16. The compound in accordance with claim 1 having the name [3-chloro-4-[3-(2-furanyl)-1,2,4-oxodiazol-5-yl]phenyl]carbamic acid, phenyl ester.

17. The compound in accordance with claim 1 having the name [3-chloro-4-[3-(2-furanyl)-1,2,4-oxadiazol-5-yl]phenyl]carbamic acid, 2,2,2-trichloroethyl ester.

* * * * *

UNITED STATES PATENT AND TRADEMARK OFFICE
CERTIFICATE OF CORRECTION

PATENT NO. : 3,976,657
DATED : August 24, 1976
INVENTOR(S) : Venkatachala L. Narayanan It is certified that error appears in the above-identified patent and that said Letters Patent are hereby corrected as shown below:

```
Column 1, line 59, "Histoplsma" should read
     -- Histoplasma --.
Column 1, line 63, delete the word "in".
Column 4, line 13, "notrophenyl" should be
     -- nitrophenyl --.
Column 4, line 14, "1,23,4" should read
     -- 1,2,4 --.
Column 4, line 64, "(0.75" should read
     -- (0.75g) --.
Column 6, line 40, "he" should read -- the --.
Column II in Table, Example 10, "carboxamide-"
     should read -- carboxamid- --.
Column IV in Table, Example 8, "H" should read
     -- H --.
Column IV in Table, Example 13, "H" should read
     -- H --.
```

Signed and Sealed this

Fourteenth Day of December 1976

[SEAL]

Attest:

RUTH C. MASON
Attesting Officer

C. MARSHALL DANN
Commissioner of Patents and Trademarks